United States Patent
Woloszynek et al.

(10) Patent No.: US 8,299,290 B2
(45) Date of Patent: Oct. 30, 2012

(54) BORON CONTAINING FUNCTIONALIZING AGENT

(75) Inventors: Robert Alan Woloszynek, Brunswick, OH (US); Stephan Rodewald, Canal Fulton, OH (US)

(73) Assignee: The Goodyear Tire & Rubber Company, Akron, OH (US)

( * ) Notice: Subject to any disclaimer, the term of this patent is extended or adjusted under 35 U.S.C. 154(b) by 0 days.

(21) Appl. No.: 13/252,616

(22) Filed: Oct. 4, 2011

(65) Prior Publication Data

US 2012/0029234 A1 Feb. 2, 2012

Related U.S. Application Data

(62) Division of application No. 12/392,415, filed on Feb. 25, 2009, now Pat. No. 8,063,152.

(60) Provisional application No. 61/069,693, filed on Mar. 17, 2008.

(51) Int. Cl.
*C07F 5/04* (2006.01)

(52) U.S. Cl. ............. 558/298; 558/286; 568/6; 564/8

(58) Field of Classification Search .......... 558/286, 558/298; 568/6; 564/8
See application file for complete search history.

(56) References Cited

U.S. PATENT DOCUMENTS

| | | | |
|---|---|---|---|
| 4,935,471 A | 6/1990 | Halasa et al. | 525/359.1 |
| 5,932,662 A | 8/1999 | Lawson et al. | 525/280 |
| 6,080,835 A | 6/2000 | Lawson et al. | 528/396 |
| 6,084,025 A | 7/2000 | Kitanura et al. | 524/575 |
| 6,344,538 B1 | 2/2002 | Sheares | 528/396 |
| 6,369,167 B1 | 4/2002 | Morita et al. | 525/342 |
| 6,627,721 B1 | 9/2003 | Rodewald et al. | 526/338 |
| 6,630,552 B1 | 10/2003 | Rodewald et al. | 526/173 |
| 6,664,328 B1 | 12/2003 | Rodewald et al. | 524/555 |
| 6,693,160 B1 | 2/2004 | Halasa et al. | 526/338 |
| 6,753,447 B2 | 6/2004 | Halasa et al. | 564/482 |
| 6,790,921 B1 | 9/2004 | Rodewald et al. | 526/173 |
| 6,812,307 B2 | 11/2004 | Halasa et al. | 526/173 |
| 6,825,306 B2 | 11/2004 | Halasa et al. | 526/279 |
| 6,901,982 B2 | 6/2005 | Halasa et al. | 152/450 |
| 6,927,269 B2 | 8/2005 | Rodewald et al. | 526/338 |
| 6,933,358 B2 | 8/2005 | Halasa et al. | 526/260 |
| 6,936,669 B2 | 8/2005 | Halasa et al. | 526/260 |
| 7,041,761 B2 | 5/2006 | Halasa et al. | 526/279 |
| 8,063,152 B2 | 11/2011 | Woloszynek et al. | 525/337 |
| 2004/0087623 A1* | 5/2004 | Gellibert et al. | 514/333 |
| 2006/0173006 A1* | 8/2006 | Sun et al. | 514/237.5 |
| 2008/0275048 A1* | 11/2008 | Frost et al. | 514/242 |

OTHER PUBLICATIONS

Zhang et al., Transition Metal Chemistry 30 (2005) 63-68.*
Chiara, J. L., Science of Synthesis 31b (2007) 1711-1723.*
Vogels et al., Canadian J. of Chemistry 79 (2001) 1115-1123.*

* cited by examiner

*Primary Examiner* — Roberto Rabago
(74) *Attorney, Agent, or Firm* — Alvin T. Rockhill

(57) ABSTRACT

The present invention relates to functionalizing agents that are particularly useful for functionalizing living rubbery polymers to make the polymer more compatible with fillers, such as carbon black and silica. These functionalizing agents are comprised of a boron containing compound having a structural formula selected from the group consisting of:

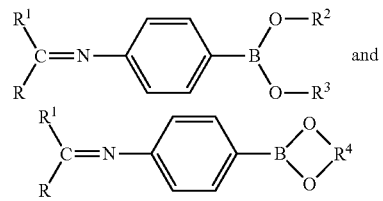

wherein R is selected from the group consisting of hydrogen atoms, alkyl groups and aryl groups, wherein $R^1$, $R^2$, and $R^3$ can be the same or different and are selected from the group consisting of alkyl groups, and aryl groups, and wherein $R^4$ represents an alkylene group or a bridging aromatic group.

20 Claims, No Drawings

BORON CONTAINING FUNCTIONALIZING AGENT

This is divisional of U.S. patent application Ser. No. 12/392,415, filed on Feb. 25, 2009, now issued as U.S. Pat. No. 8,063,152, which claims the benefit of U.S. Provisional Application Ser. No. 61/069,693, filed on Mar. 17, 2008.

BACKGROUND OF THE INVENTION

It is highly desirable for rubbery polymers that are used in manufacturing tires, hoses, power transmission belts and other industrial products to have good compatibility with fillers, such as rubber reinforcing carbon black and amorphous rubber reinforcing silica. In cases where other materials, such as clay or starch, are used as reinforcing fillers for the rubber, it is also beneficial for the rubbery polymer to have good compatibility therewith. To attain improved interaction with fillers, such rubbery polymers can be functionalized with various compounds such as amines. For instance, U.S. Pat. No. 4,935,471 discloses a process for preparing a polydiene having a high level of affinity for carbon black which comprises reacting a metal terminated polydiene with a capping agent selected from the group consisting of (a) halogenated nitrites having the structural formula X-A-C≡N, wherein X represents a halogen atom and wherein A represents an alkylene group containing from 1 to 20 carbon atoms, (b) heterocyclic aromatic nitrogen containing compounds, and (c) alkyl benzoates.

The capping agents disclosed by U.S. Pat. No. 4,935,471 react with metal terminated polydienes and replace the metal with a terminal cyanide group, a heterocyclic aromatic nitrogen containing group or a terminal group which is derived from an alkyl benzoate. For example, if the metal terminated polydiene is capped with a nitrile, it will result in the polydiene chains being terminated with cyanide groups. The use of heterocyclic aromatic nitrogen containing compounds as capping agents can result in the polydiene chains being terminated with a pyrrolyl group, an imidazolyl group, a pyrazolyl group, a pyridyl group, a pyrazinyl group, a pyrimidinyl group, a pyridazinyl group, an indolizinyl group, an isoindolyl group, a 3-H-indolyl group, a cinnolinyl group, a pteridinyl group, a β-carbolinyl group, a perimidinyl group, a phenanthrolinyl group or the like.

U.S. Pat. No. 4,935,471 also discloses that lithium amides are highly preferred initiators because they can be used to prepare polydienes which are terminated with polar groups at both ends of their polymer chains. The extra polar functionality provided by lithium amides results in increased interaction with carbon black resulting in better polymer-carbon black dispersion. The lithium amides disclosed by U.S. Pat. No. 4,935,471 include lithium pyrrolidide. U.S. Pat. No. 4,935,471 also indicates that preferred initiators include amino alkyl lithium compounds of the structural formula:

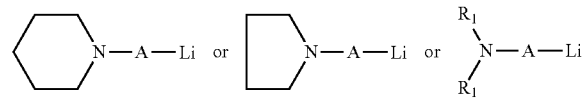

wherein A represents an alkylene group containing from 1 to 20 carbon atoms, and wherein $R_1$ and $R_2$ can be the same or different and represent alkyl groups containing from 1 to 20 carbon atoms.

It is also desirable for synthetic rubbers to exhibit low levels of hysteresis. This is particularly important in the case of rubbers that are used in tire tread compounds. Such polymers are normally compounded with sulfur, carbon black, accelerators, antidegradants and other desired rubber chemicals and are then subsequently vulcanized or cured into the form of a useful article. It has been established that the physical properties of such cured rubbers depend upon the degree to which the carbon black is homogeneously dispersed throughout the polydiene rubber. This is in turn related to the level of affinity that carbon black has for the rubber. This can be of practical importance in improving the physical characteristics of rubber articles that are made utilizing polydiene rubbers. For example, the rolling resistance and tread wear characteristics of tires can be improved by increasing the affinity of carbon black to the rubbery polymers utilized therein. Therefore, it would be highly desirable to improve the affinity of a given polydiene rubber for carbon black and/or silica. This is because a better dispersion of carbon black throughout polydiene rubbers which are utilized in compounding tire tread compositions results in a lower hysteresis value and consequently tires made therefrom have lower rolling resistance. It is also known that a major source of hysteresis is due to polymer chain ends that are not capable of full elastic recovery. Accordingly, improving the affinity of the rubber chain ends to the filler is extremely important in reducing hysteresis.

U.S. Pat. No. 6,080,835 discloses a functionalized elastomer comprising: a functional group defined by the formula:

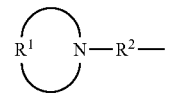

where $R^1$ is a selected from the group consisting of a divalent alkylene group, an oxy-alkylene group, an amino alkylene group, and a substituted alkylene group, each group having from about 6 to about 20 carbon atoms, $R^2$ is covalently bonded to the elastomer and is selected from the group consisting of a linear-alkylene group, a branched-alkylene group, and a cyclo-alkylene group, each group having from about 2 to about 20 carbon atoms.

U.S. Pat. No. 5,932,662 discloses a method of preparing a polymer comprising: polymerizing one or more anionically polymerizable monomers in a solvent in the presence of a polymerization initiator of the formula:

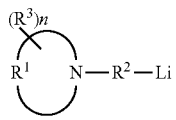

wherein $R^1$ is a divalent alkylene, an oxy- or amino-alkylene having from 6 to about 20 carbon atoms, wherein $R^2$ is a linear-alkylene, branched-alkylene, or cyclo-alkylene having from about 2 to about 20 carbon atoms, wherein Li is a lithium atom bonded directly to a carbon atom of $R^2$; and wherein $R^3$ is a tertiary amino, an alkyl having from about 1 to about 12 carbon atoms, an aryl having from about 6 to about 20 carbon atoms, an alkaryl having from about 7 to about 20 carbon atoms, an alkenyl having from about 2 to about 12 carbon atoms, a cycloalkyl having from about 5 to about 20 carbon atoms, a cycloalkenyl having from about 5 to about 20 carbon atoms, a bicycloalkyl having from about 6 to about 20 carbon atoms, and, a bicycloalkenyl having from about 6 to about 20 carbon atoms, and where n represents an integer of from 0 to about 10.

U.S. Pat. No. 6,084,025 discloses a functionalized polymer prepared by a process comprising the steps of: preparing a solution of a cyclic amine compound, an organolithium compound, and from 3 to about 300 equivalents, based upon one equivalent of lithium, of a monomer selected from vinyl aromatic monomers, and mixtures thereof, where said cyclic amine compound is defined by the formula:

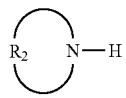

where $R_2$ is selected from the group consisting of an alkylene, substituted alkylene, bicycloalkane, and oxy-alkylene group or N-alkylamino-alkylene group having from about 3 to about 16 methylene groups, wherein N represents a nitrogen atom, and wherein H represents a hydrogen atom, thereby forming a polymerization initiator having the formula $A(SOL)_y Li$, where Li is a lithium atom, SOL is a divalent hydrocarbon group having from 3 to about 300 polymerized monomeric units, y is from 0.5 to about 3, and A is a cyclic amine radical derived from said cyclic amine; charging the solution containing $A(SOL)_y Li$ with from about 0.01 to about 2 equivalents per equivalent of lithium of a chelating reagent, and an organic alkali metal compound selected from compounds having the formula $R_4 OM$, $R_5 C(O)OM$, $R_6 R_7 NM$, and $R_8 SO_3 M$, where $R_4$, $R_5$, $R_6$, $R_7$, and $R_8$ are each selected from alkyls, cycloalkyls, alkenyls, aryls, or phenyls, having from 1 to about 12 carbon atoms; and where M is Na, K, Rb or Cs, and sufficient monomer to form a living polymeric structure; and quenching the living polymeric structure.

In the initiator systems of U.S. Pat. No. 6,084,025 a chelating reagent can be employed to help prevent heterogeneous polymerization. The reagents that are reported as being useful include tetramethylethylenediamine (TMEDA), oxolanyl cyclic acetals, and cyclic oligomeric oxolanyl alkanes. The oligomeric oxolanyl alkanes may be represented by the structural formula:

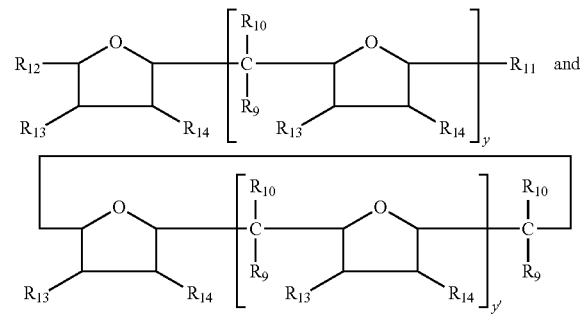

wherein $R_9$ and $R_{10}$ independently are hydrogen or an alkyl group and the total number of carbon atoms in $-CR_9 R_{10}-$ ranges between one and nine inclusive; wherein y is an integer of 1 to 5 inclusive; wherein y' is an integer of 3 to 5 inclusive, and wherein $R_{11}$, $R_{12}$, $R_{13}$, and $R_{14}$ are independently $-H$ or $-C_n H_{2n+1}$, and wherein n represents an integer within the range of 1 to 6.

U.S. Pat. No. 6,344,538 discloses functionalized monomers and polymerized functionalized monomers selected from the group consisting of 2-(N,N-dimethylaminomethyl)-1,3-butadiene, 2-(N,N-diethylaminomethyl)-1,3-butadiene, 2-(N,N-di-n-propylaminomethyl)-1,3-butadiene, 2-(cyanomethyl)-1,3-butadiene, 2-(aminomethyl)-1,3-butadiene, 2-(hydroxymethyl)-1,3-butadiene, 2-(carboxymethy)-1,3-butadiene, 2-(acetoxymethyl)-1,3-butadiene, 2-(2-alkoxy-2-oxoethyl)-1,3-butadiene, 2,3-bis(cyanomethyl)-1,3-butadiene, 2,3-bis(dialkylaminomethyl)-1,3-butadiene, 2,3-bis(4-ethoxy-4-4-oxobutyl)-1,3-butadiene and 2,3-bis(3-cyanopropyl)-1,3-butadiene, and methods for preparing such functionalized diene monomers and polymers.

U.S. Pat. No. 6,627,721, U.S. Pat. No. 6,630,552, U.S. Pat. No. 6,664,328, U.S. Pat. No. 6,790,921, U.S. Pat. No. 6,812,307, and U.S. Pat. No. 6,927,269 relate to rubbery polymers having functionality for better interaction with fillers incorporated therein through the use of functionalized vinyl aromatic monomers. For instance, U.S. Pat. No. 6,812,307 discloses rubbery polymers that contain functionalized monomers of the structural formula:

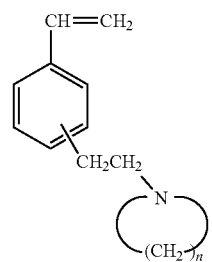

wherein n represents an integer from 4 to about 10, into rubbery polymers.

U.S. Pat. No. 6,627,721 and U.S. Pat. No. 6,630,552 disclose rubbery polymers that are comprised of repeat units that are derived from (1) at least one conjugated diolefin monomer, and (2) at least one functionalized monomer having of the structural formula:

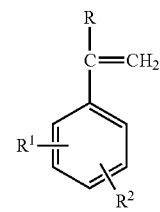

wherein R represents an alkyl group containing from 1 to about 10 carbon atoms or a hydrogen atom, and wherein $R^1$ and $R^2$ can be the same or different and represent hydrogen atoms or a moiety selected from the group consisting of

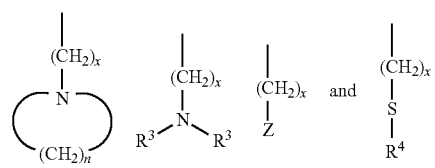

wherein R³ groups can be the same or different and represent alkyl groups containing from 1 to about 10 carbon atoms, aryl groups, allyl groups, and alkyloxy groups of the structural formula —(CH₂)_y—O—(CH₂)_z—CH₃, wherein Z represents a nitrogen containing heterocyclic compound, wherein R⁴ represents a member selected from the group consisting of alkyl groups containing from 1 to about 10 carbon atoms, aryl groups, and allyl groups, and wherein n, x, y and z represents integers from 1 to about 10, with the proviso that R¹ and R² can not both be hydrogen atoms.

U.S. Pat. No. 6,825,306, U.S. Pat. No. 6,901,982, and U.S. Pat. No. 7,041,761 disclose a rubbery polymer having improved compatibility with fillers which is comprised of repeat units that are derived from (1) at least one conjugated diolefin monomer, and (2) at least one functionalized monomer of the structural formula:

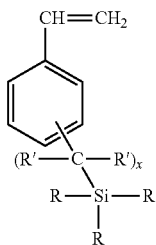

wherein the R' groups in repeat units and in different repeat units can be the same or different and represent hydrogen atoms or alkyl groups containing from 1 to about 4 carbon atoms, wherein x represents an integer from 1 to about 10, and wherein the R groups in repeat units and in different repeat units can be the same or different and represent alkyl groups containing from 1 to about 10 carbon atoms or alkoxy groups containing from 1 to about 10 carbon atoms.

U.S. Pat. No. 6,693,160, U.S. Pat. No. 6,753,447, U.S. Pat. No. 6,933,358, and U.S. Pat. No. 6,936,669 also disclose the use of monomers that can be incorporated into rubbery polymers to improve compatibility with fillers. These polymers include those that are of the structural formula:

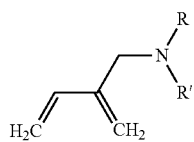

wherein R and R' can be the same or different and represent allyl, alkoxyl or alkyl groups containing from 1 to about 10 carbon atoms, and

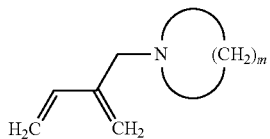

wherein m represents an integer from about 4 to about 10.

U.S. Pat. No. 6,369,167 B1 discloses a modified diene polymer capable of creating good reinforcing characteristics and filler dispersing effect independently of the kinds of the filler as well as a process for making the polymer and to provide a rubber composition having good fracture characteristics, wear resistance, and low exothermicity without the impairment of wet performance. The above-described object can be achieved by a process for making the polymer, said process comprising the steps of polymerizing or copolymerizing a conjugated diene monomer by using an organolithium compound as an initiator in a hydrocarbon solvent and thereafter allowing the active termination of the polymer to react with a compound having an alkylideneamino group represented by the formula:

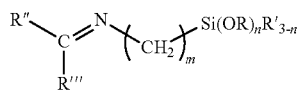

wherein R, R', R", and R''' each represent a group having 1 to 18 carbon atoms selected from the group consisting of: an alkyl group, an allyl group, or an aryl group; and m and n are integers of from 1 to 20 and from 1 to 3, respectively.

SUMMARY OF THE INVENTION

The present invention relates to functionalizing agents that can be used to make rubbery polymers more compatible with fillers that are typically used in reinforcing rubber compounds, such as carbon black and silica. These functionalizing agents can be added to the cement of a living rubbery polymer and react therewith to incorporate a functional group at the terminal end of its polymer chains. Such living rubbery polymers are polymer chains that are capable of further polymerization by virtue of having reactive chain ends which are typically anions associated with cationic entities, such as cations of Group I metals or cationic organometalic species. This functionalization results in the rubbery polymer exhibiting a lower level of hysteresis without sacrificing other desirable physical properties. Accordingly, rubbery polymers that are functionalized with these agents can be utilized in manufacturing tires that offer improved rolling resistance (better fuel economy) realized because the functionalized monomers of this invention improve the compatibility of the rubber with the types of fillers, such as carbon black and silica.

The present invention more specifically discloses a functionalizing agent which is comprised of a boron containing compound having a structural formula selected from the group consisting of:

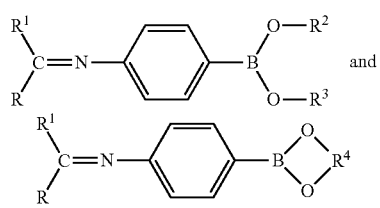

wherein R is selected from the group consisting of hydrogen atoms, alkyl groups and aryl groups, wherein R¹, R², and R³ can be the same or different and are selected from the group consisting of alkyl groups, and aryl groups, and wherein R⁴ represents an alkylene group or a bridging aromatic group.

The present invention further discloses a rubbery polymer having a structural formula selected from the group consisting of:

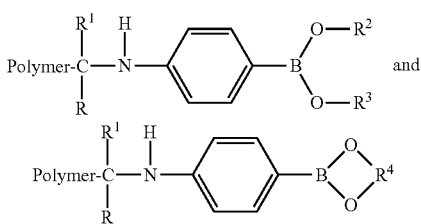

wherein Polymer represents the polymer chain of a rubbery polymer, wherein R is selected from the group consisting of hydrogen atoms, alkyl groups and aryl groups, wherein $R^1$, $R^2$, and $R^3$ can be the same or different and are selected from the group consisting of alkyl groups, and aryl groups, and wherein $R^4$ represents an alkylene group or a bridging aromatic group.

The subject invention also reveals a rubber composition which is comprised of (I) a conventional rubbery polymer which is comprised of repeat units that are derived from at least one conjugated diolefin monomer, and (II) a rubbery polymer having a structural formula selected from the group consisting of:

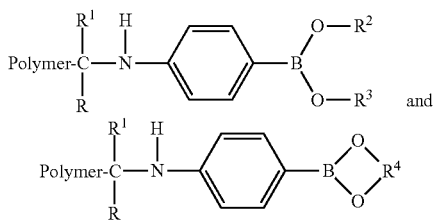

wherein Polymer represents the polymer chain of a rubbery polymer, wherein R is selected from the group consisting of hydrogen atoms, alkyl groups and aryl groups, wherein $R^1$, $R^2$, and $R^3$ can be the same or different and are selected from the group consisting of alkyl groups, and aryl groups, and wherein $R^4$ represents an alkylene group or a bridging aromatic group.

The present invention also discloses a tire which is comprised of a generally toroidal-shaped carcass with an outer circumferential tread, two spaced beads, at least one ply extending from bead to bead and sidewalls extending radially from and connecting said tread to said beads, wherein said tread is adapted to be ground-contacting, and wherein said tread is comprised of (I) a filler, (II) a conventional rubbery polymer which is comprised of repeat units that are derived from at least one conjugated diolefin monomer, and (III) a rubbery polymer having a structural formula selected from the group consisting of:

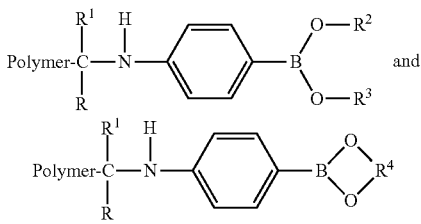

wherein Polymer represents the polymer chain of a rubbery polymer, wherein R is selected from the group consisting of hydrogen atoms, alkyl groups and aryl groups, wherein $R^1$, $R^2$, and $R^3$ can be the same or different and are selected from the group consisting of alkyl groups, and aryl groups, and wherein $R^4$ represents an alkylene group or a bridging aromatic group.

The subject invention further reveals a process for preparing a functionalized rubbery polymer which comprises (1) polymerizing a conjugated diolefin monomer by anionic polymerization to produce a living rubbery polymer, and (2) adding a functionalizing agent to the living rubbery polymer to produce the functionalized rubbery polymer, wherein the functionalizing agent has a structural formula selected from the group consisting of:

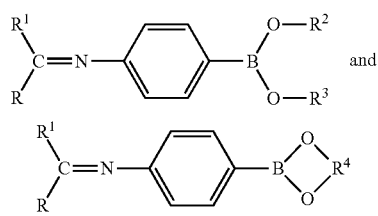

wherein R is selected from the group consisting of hydrogen atoms, alkyl groups and aryl groups, wherein $R^1$, $R^2$, and $R^3$ can be the same or different and are selected from the group consisting of alkyl groups, and aryl groups, and wherein $R^4$ represents an alkylene group or a bridging aromatic group.

The present invention also discloses a process for synthesizing a boron containing functionalizing agent which comprises reacting a boronic ester with a carbonyl compound to produce the boron containing functionalizing agent, wherein the boronic ester has a structural formula selected from the group consisting of:

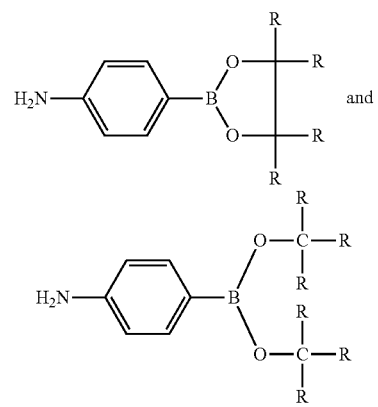

wherein R represents alkyl groups or hydrogen atoms, wherein the R groups in the boronic ester can be the same or different, wherein the boron containing functionalizing agent has a structural formula selected from the group consisting of

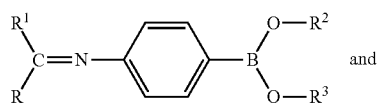

-continued

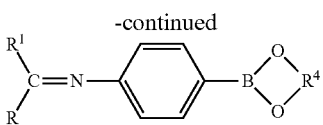

wherein R is selected from the group consisting of hydrogen atoms, alkyl groups and aryl groups, wherein $R^1$, $R^2$, and $R^3$ can be the same or different and are selected from the group consisting of alkyl groups, and aryl groups, and wherein $R^4$ represents an alkylene group or a bridging aromatic group.

DETAILED DESCRIPTION OF THE INVENTION

The functionalizing agents of this invention are of the structural formula:

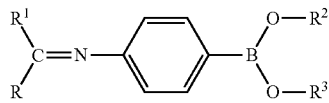

or are of the structural formula:

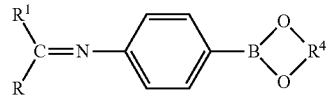

wherein R is selected from the group consisting of hydrogen atoms, alkyl groups and aryl groups, wherein $R^1$, $R^2$, and $R^3$ can be the same or different and are selected from the group consisting of alkyl groups, and aryl groups, and wherein $R^4$ represents an alkylene group or a bridging aromatic group.

The alkyl groups in these functionalizing agents will typically contain from 1 to about 20 carbon atoms, will more typically contain from 1 to 8 carbon atoms, and will preferably contain from 1 to 4 carbon atoms. $R^2$ and $R^3$ will normally represent methyl groups (—$CH_3$). The aryl groups in these functionalizing agents will typically contain from 5 to about 20 carbon atoms and will more typically contain from 6 to 12 carbon atoms. $R^1$ preferably represents a phenyl group and R preferably represents a hydrogen atom.

$R^4$ typically represents an alkylene group that can be straight chained or branched or a bridging aromatic group that contains from 6 to 30 carbon atoms. In cases where $R^4$ represents an alkylene group it will typically contain from 2 to about 20 carbon atoms and will more typically contain from 2 to 6 carbon atoms. For instance, $R^4$ can represent a straight chained alkylene group of the structural formula: —$(CH_2)_n$— wherein n represents an integer from 2 to about 20. It is typically preferred for n to represent an integer from 2 to 6 with it being most preferred for n to represent 2.

The bridging aromatic groups that can represent $R^4$ have a favorable geometry to allow bonding with the two oxygen atoms that are directly bonded to the boron atom in the functionalizing agent. The aromatic bridging group will typically contain from 6 to 30 carbon atoms and will more typically contain from 6 to 20 carbon atoms. The aromatic bridging group will normally contain from 6 to 12 carbon atoms. The aromatic ring in the bridging aromatic group can be a benzene ring, a naphthalene ring structure, an anthracene ring structure, a phenanthrene ring structure, a pentalene ring structure, an indene ring structure, an azulene ring structure, a heptalene ring structure, a biphenylene ring structure, a s-indacene ring structure, a fluorine ring structure, an acenaphthylene ring structure, an acephenanthtylene ring structure, a chrysene ring structure, a pyrene ring structure, a naphthacene ring structure, a triphenylmethane ring structure, a tetraphenylmethane ring structure, a stilbene ring structure, a biphenyl ring structure, and the like. Normally, the bridge will be through adjacent carbon atoms on the aromatic ring structure. Some representative examples of bridging aromatic groups that can function in this capacity are of the following structural formulas:

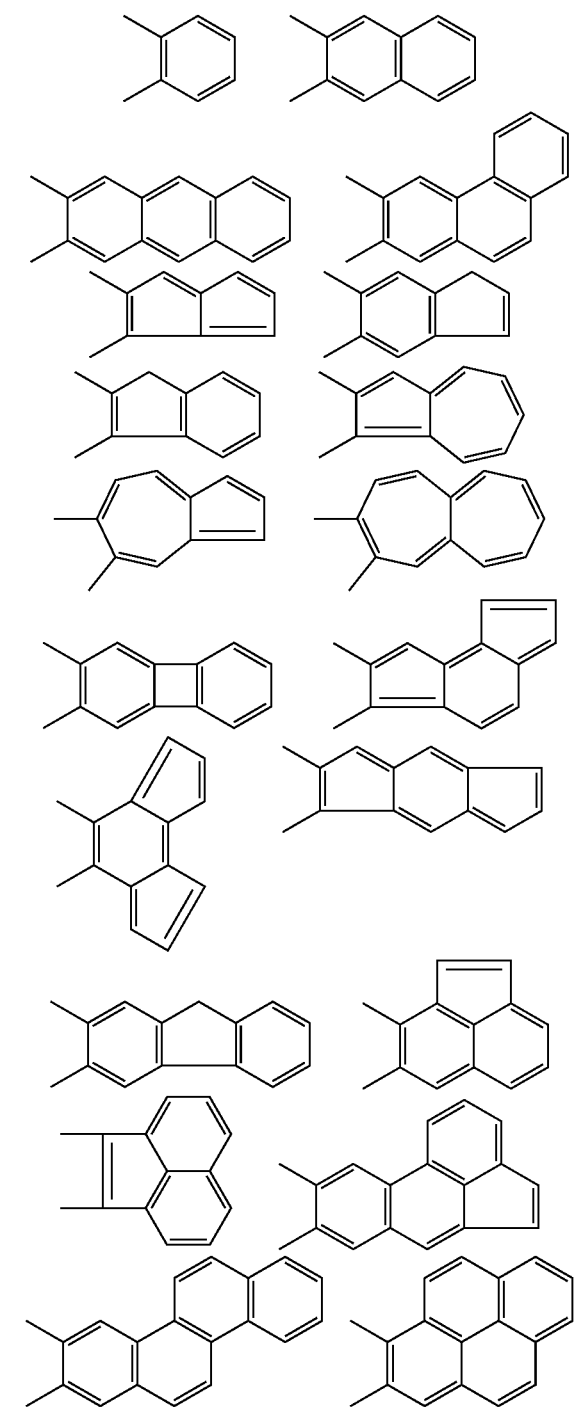

-continued

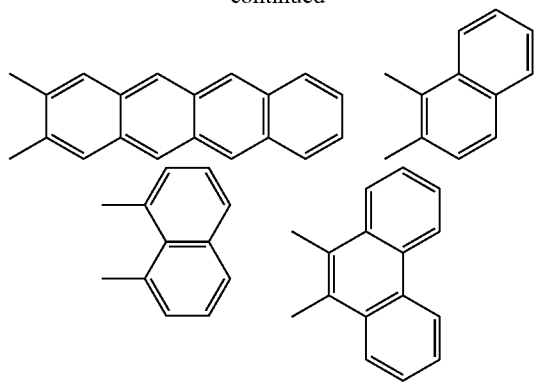

It is highly preferred for the functionalizing agent to be of the structural formula:

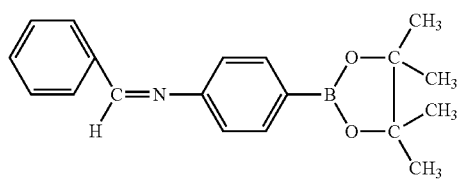

The functionalizing agents of this invention can be synthesized by a two step process which involves (1) reacting a boronic acid with an alcohol or diol via a condensation reaction to produce a boronic ester, and (2) further reacting the boronic ester with a carbonyl compound (an aldehyde or a ketone) to produce the functionalizing agent. In cases where the boronic acid is reacted with a diol this reaction scheme can be depicted by the general reaction scheme:

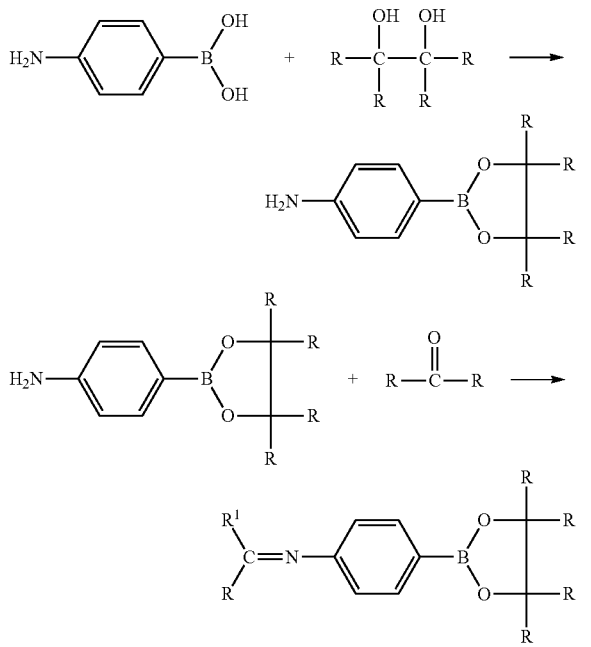

wherein the R groups can be the same or different and represent alkyl groups or hydrogen atoms, and wherein $R^1$ represents an aryl group or an alkyl group.

Aromatic diols can be used to synthesize functionalizing agents having aromatic bridging groups. For instance, the use of catechol (1,2-dihydroxybenzene) as the aromatic diol can be depicted by the general reaction scheme:

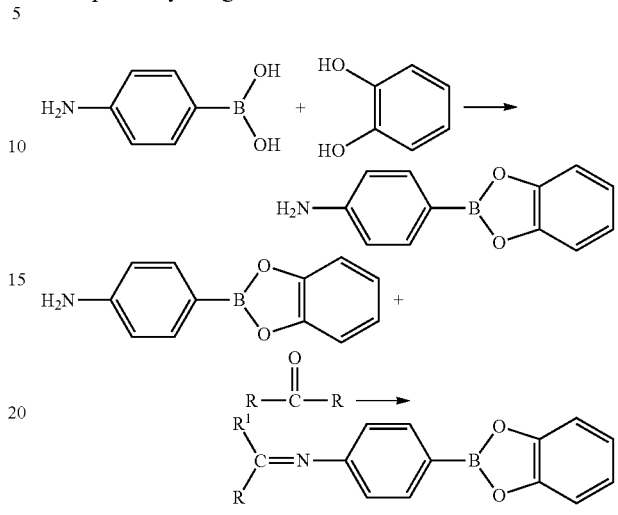

wherein the R groups can be the same or different and represent alkyl groups or hydrogen atoms, and wherein $R^1$ represents an aryl group or an alkyl group.

In cases where the boronic acid is reacted with an alcohol this reaction can be depicted by the general reaction scheme:

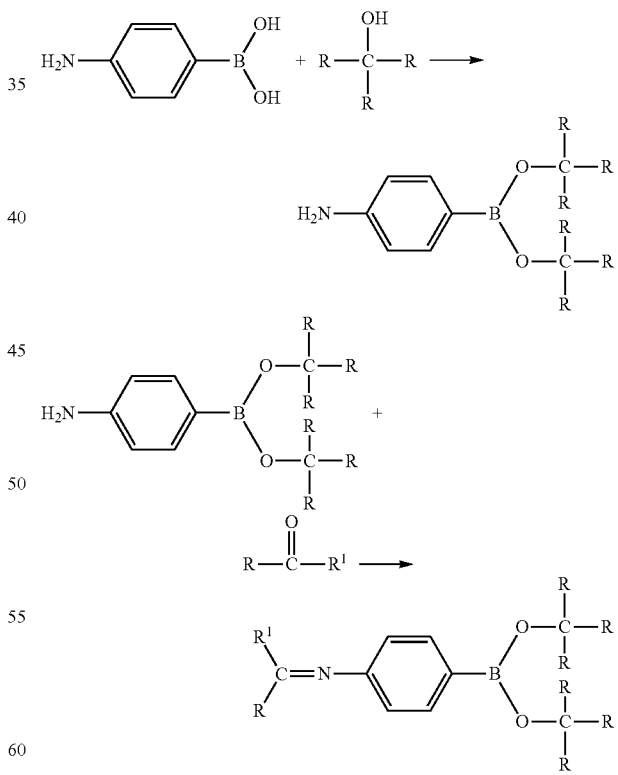

wherein the R groups can be the same or different and represent alkyl groups or hydrogen atoms.

Certain boronic esters that are useful in the synthesis of functionalizing agents of this invention are available from commercial suppliers. For instance, 4-aminophenylboronic acid pinacol ester is sold by the Sigma-Aldrich Company. In any case, 4-aminophenylboronic acid pinacol ester can be made by the following reaction utilizing pinacol (2,3-dimethyl-2,3-butanediol) as the diol:

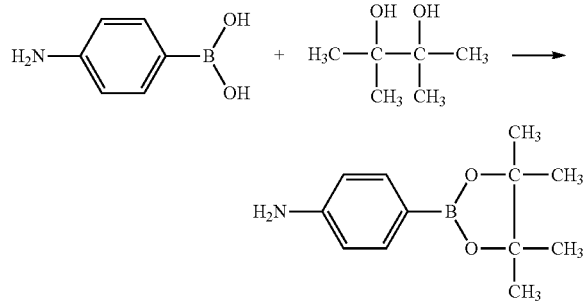

The 4-aminophenylboronic acid pinacol ester can then used in synthesizing p-benzyliminephenylboronic acid pinacol ester according to the following reaction:

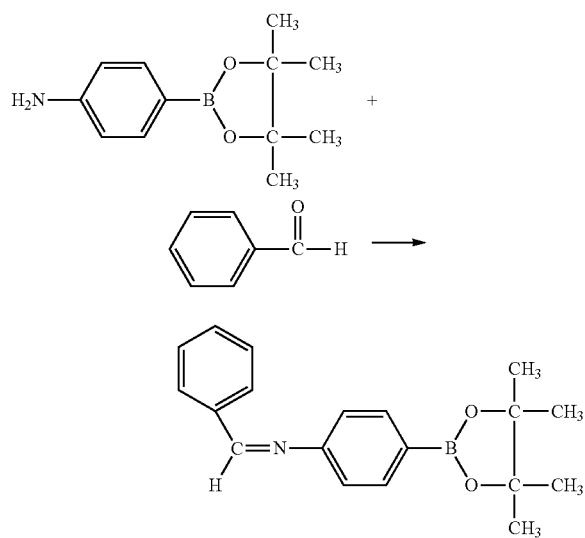

It is typically advantageous to conduct this reaction in an inert organic solvent under an inert gas atmosphere at an elevated temperature. This reaction will typically be conducted at a temperature which is within the range of about 50° C. to about 150° C. and will more typically be conducted at a temperature which is within the range of 80° C. to 120° C.

Virtually any type of synthetic rubber synthesized by anionic polymerization can be functionalized with the functionalizing agents of this invention. This can be accomplished by simply adding the boron containing functionalizing agent to the living rubbery polymer. This will typically be done by adding the boron containing functionalizing agent to a solution of the living rubbery polymer before its living polymer chain ends are killed. The boron containing functionalizing agent reacts with living polymer chain ends on a 1:1 molar basis. For instance, p-benzyliminephenylboronic acid pinacol ester can be used to functionalize a living lithium terminated rubbery polymer according to the following reaction:

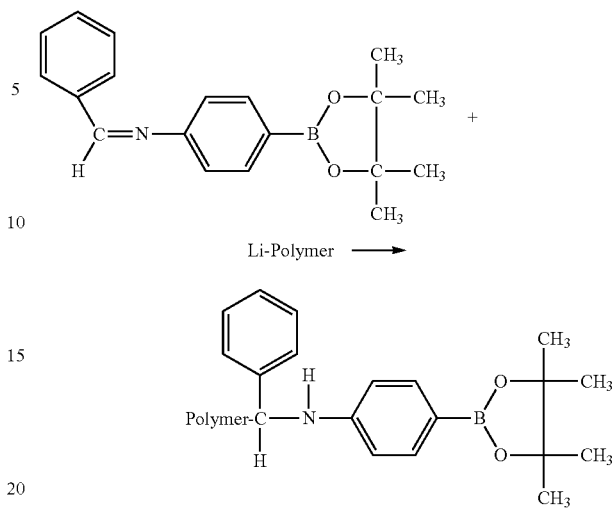

wherein Polymer represents a polymer chain of the rubbery polymer.

The boronic ester functionality of the functionalizing agents of this invention will typically undergo protonolysis which results in the formation of boronic acids. Such protonolysis can occur after the functionalizing agent has been bound to a rubbery polymer. For a rubbery polymer that has been functionalized with p-benzyliminephenylboronic acid pinacol ester this protonolysis reaction can be depicted as follows:

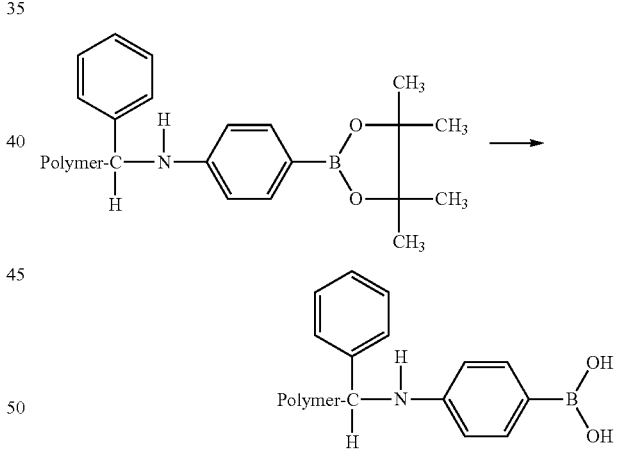

wherein Polymer designates a polymer chain of a rubbery polymer. Optimally, one mole of the functionalizing agent will be added per mole of living lithium chain ends in the rubbery polymer being functionalized. Normally, the molar amount of functionalizing agent utilized will be equivalent to the molar amount of lithium initiator used in synthesizing the rubbery polymer. Typically, the molar ratio of functionalizing agent to living lithium chain ends will be within the range of 0.7:1 to 1.1:1 and will more typically be within the range of 0.9:1 to 1.02:1.

The functionalized rubbery polymer can react with hydroxyl groups (—OH) on particles of silica in accordance with the following a condensation reaction:

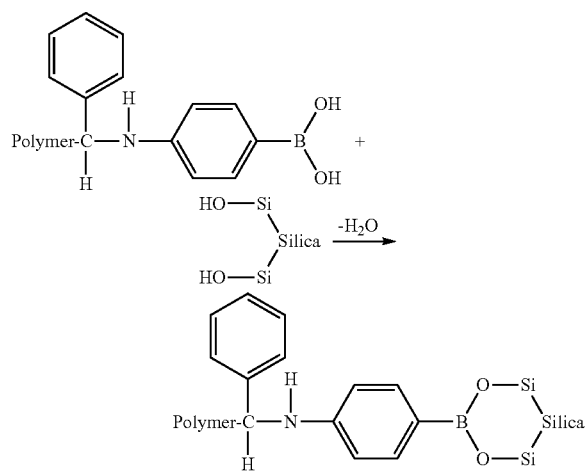

wherein Silica represents a particle of rubber reinforcing silica. As can be seen this reaction produces water and covalently bonds the rubbery polymer to the silica particles. This results in the rubber having excellent compatibility with the rubber reinforcing silica.

In the practice of this invention, the polymerization of monomer and recovery of polymer are suitably carried out according to various methods suitable for diene monomer polymerization processes. In any case, at least one conjugated diolefin monomer, such as 1,3-butadiene or isoprene, will be polymerized and optionally other monomers that are copolymerizable with conjugated diolefin monomers, such as vinyl aromatic monomers, can also be included in the polymerization. The conjugated diolefin monomers which can be utilized in the synthesis of rubbery polymers which can be coupled in accordance with this invention generally contain from 4 to 12 carbon atoms. Those containing from 4 to 8 carbon atoms are generally preferred for commercial purposes. For similar reasons, 1,3-butadiene and isoprene are the most commonly utilized conjugated diolefin monomers. Some additional conjugated diolefin monomers that can be utilized include 2,3-dimethyl-1,3-butadiene, piperylene, 3-butyl-1,3-octadiene, 2-phenyl-1,3-butadiene, and the like, alone or in admixture.

The vinyl aromatic monomers that can be used typically contain from 8 to 20 carbon atoms. Usually, the vinyl aromatic monomer will contain from 8 to 14 carbon atoms. Some examples of vinyl aromatic monomers that can be utilized include styrene, 1-vinylnaphthalene, 2-vinylnaphthalene, α-methylstyrene, 4-phenylstyrene, 3-methylstyrene and the like. Styrene and α-methylstyrene are preferred vinyl aromatic monomers for copolymerization with the conjugated diolefin monomers. The most widely used vinyl aromatic monomer is styrene.

Rubbery polymers which are copolymers of one or more diene monomers with one or more other ethylenically unsaturated monomers will normally contain from about 50 weight percent to about 99 weight percent conjugated diolefin monomers and from about 1 weight percent to about 50 weight percent of the other ethylenically unsaturated monomers in addition to the conjugated diolefin monomers. For example, copolymers of conjugated diolefin monomers with vinylaromatic monomers, such as styrene-butadiene rubbers which contain from 50 to 95 weight percent conjugated diolefin monomers and from 5 to 50 weight percent vinylaromatic monomers, are useful in many applications.

Some representative examples of rubbery polymers that can be functionalized with the functionalized monomers of this invention include polybutadiene homopolymer rubber, polyisoprene homopolymer rubber, styrene-butadiene rubber (SBR), α-methylstyrene-butadiene rubber, α-methylstyrene-isoprene rubber, styrene-isoprene-butadiene rubber (SIBR), styrene-isoprene rubber (SIR), isoprene-butadiene rubber (IBR), α-methylstyrene-isoprene-butadiene rubber and α-methylstyrene-styrene-isoprene-butadiene rubber. In cases where the rubbery polymer is comprised of repeat units that are derived from two or more monomers, the repeat units which are derived from the different monomers will normally be distributed in an essentially random manner. The repeat units that are derived from the monomers differ from the monomer in that a double bond is normally consumed in by the polymerization reaction.

The polymerizations used in synthesizing the living rubbery polymers that can be functionalized in accordance with this invention can be conducted in batch, semi-continuous, or continuous operations under conditions that exclude air and other atmospheric impurities, particularly oxygen and moisture. The polymerizations of the invention may also be carried out in a number of different polymerization reactor systems, including but not limited to bulk polymerization, vapor phase polymerization, and solution polymerization systems. The commercially preferred method of polymerization is typically solution polymerization.

The polymerization reaction will be initiated with an anionic initiator, such as an organo-lithium compound. The organo-lithium compound will typically be an alkyl lithium compound that contains from 1 to about 8 carbon atoms, such as n-butyl lithium.

The organolithium compounds which are preferred can be represented by the formula: R—Li, wherein R represents a hydrocarbyl radical containing from 1 to about 20 carbon atoms. Generally, such monofunctional organolithium compounds will contain from 1 to about 10 carbon atoms. Some representative examples of organolithium compounds which can be employed include methyllithium, ethyllithium, isopropyllithium, n-butyllithium, sec-butyllithium, n-octyllithium, tert-octyllithium, n-decyllithium, phenyllithium, 1-napthyllithium, 4-butylphenyllithium, p-tolyllithium, 1-naphthyllithium, 4-butylphenyllithium, p-tolyllithium, 4-phenylbutyllithium, cyclohexyllithium, 4-butylcyclohexyllithium, and 4-cyclohexylbutyllithium. Organo-monolithium compounds, such as alkyllithium compounds and aryllithium compounds, are usually employed. Some representative examples of preferred organo monolithium compounds that can be utilized include ethylaluminum, isopropylaluminum, n-butyllithium, secondary-butyllithium, normal-hexyllithium, tertiary-octyllithium, phenyllithium, 2-napthyllithium, 4-butylphenyllithium, 4-phenylbutyllithium, cyclohexyllithium, and the like. Normal-butyllithium and secondary-butyllithium are highly preferred lithium initiators.

The amount of lithium catalyst utilized will vary from one organolithium compound to another and with the molecular weight that is desired for the rubber being synthesized. As a general rule, in all anionic polymerizations the molecular weight (Mooney viscosity) of the polymer produced is inversely proportional to the amount of catalyst utilized. Normally, from about 0.01 phm (parts per hundred parts by weight of monomer) to 1 phm of the lithium catalyst will be employed. In most cases, from 0.01 phm to 0.1 phm of the lithium catalyst will be employed with it being preferred to utilize 0.025 phm to 0.07 phm of the lithium catalyst.

Typically, from about 5 weight percent to about 35 weight percent of the monomer will be charged into the polymerization medium (based upon the total weight of the polymerization medium including the organic solvent and monomer). In most cases, it will be preferred for the polymerization medium to contain from about 10 weight percent to about 30 weight percent monomer. It is typically more preferred for the polymerization medium to contain from about 15 weight percent to about 28 weight percent monomer. It is typically most preferred for the polymerization medium to contain from about 20 weight percent to about 25 weight percent monomer.

The solution polymerizations of this invention will be carried out in a suitable solvent that is liquid under the conditions of reaction and relatively inert. The solvent may have the same number of carbon atoms per molecule as the diene reactant or it may be in a different boiling range. Such hydrocarbon solvents are comprised of one or more aromatic, paraffinic or cycloparaffinic compounds. These solvents will normally contain from about 4 to about 10 carbon atoms per molecule and will be liquid under the conditions of the polymerization. Some representative examples of suitable organic solvents include pentane, isooctane, cyclohexane, methylcyclohexane, isohexane, n-heptane, n-octane, n-hexane, benzene, toluene, xylene, ethylbenzene, diethylbenzene, isobutylbenzene, petroleum ether, kerosene, petroleum spirits, petroleum naphtha, and the like, alone or in admixture. Preferred solvents are alkane and cycloalkane hydrocarbons. Suitable solvents are, for example, hexane, cyclohexane, methylcyclohexane, or various saturated hydrocarbon mixtures. Aromatic hydrocarbons such as benzene, toluene, isopropylbenzene, xylene, or halogenated aromatic compounds such as chlorobenzene, bromobenzene, or orthodichlorobenzene can also be employed. Other useful solvents include tetrahydrofuran and dioxane.

The polymerization temperature will normally be within the range of about 5° C. to about 100° C. For practical reasons and to attain the desired microstructure the polymerization temperature will preferably be within the range of about 40° C. to about 90° C. Polymerization temperatures within the range of about 60° C. to about 90° C. are most preferred. The microstructure of the rubbery polymer is somewhat dependent upon the polymerization temperature. For example, it is known that higher temperatures result in lower vinyl contents (lower levels of 1,2-microstructure in the case of polybutadiene rubber). Accordingly, the polymerization temperature will be determined with the desired microstructure of the rubber polymer being synthesized being kept in mind.

The rubbery polymer can be made by solution polymerization in a batch process in a continuous process by continuously charging at least one conjugated diolefin monomer, the functionalized monomer, and any additional monomers into a polymerization zone. The polymerization zone will typically be a polymerization reactor or a series of polymerization reactors. The polymerization zone will normally provide agitation to keep the monomers, polymer, initiator, and modifier well dispersed throughout the organic solvent the polymerization zone. Such continuous polymerizations are typically conducted in a multiple reactor system. The rubbery polymer synthesized is continuously withdrawn from the polymerization zone. The monomer conversion attained in the polymerization zone will normally be at least about 85 percent. It is preferred for the monomer conversion to be at least about 90 percent.

The polymerization process of this invention is normally conducted in the presence of polar modifiers, such as alkyltetrahydrofurfuryl ethers. Some representative examples of specific polar modifiers that can be used include methyltetrahydrofurfuryl ether, ethyltetrahydrofurfuryl ether, propyltetrahydrofurfuryl ether, butyltetrahydrofurfuryl ether, hexyltetrahydrofurfuryl ether, octyltetrahydrofurfuryl ether, dodecyltetrahydrofurfuryl ether, diethyl ether, di-n-propyl ether, diisopropyl ether, di-n-butyl ether, tetrahydrofuran, dioxane, ethylene glycol dimethyl ether, ethylene glycol diethyl ether, diethylene glycol dimethyl ether, diethylene glycol diethyl ether, triethylene glycol dimethyl ether, trimethylamine, triethylamine, N,N,N',N'-tetramethylethylenediamine, N-methyl morpholine, N-ethyl morpholine, or N-phenyl morpholine.

The polar modifier will typically be employed at a level wherein the molar ratio of the polar modifier to the lithium initiator is within the range of about 0.01:1 to about 5:1. The molar ratio of the polar modifier to the lithium initiator will more typically be within the range of about 0.1:1 to about 4:1. It is generally preferred for the molar ratio of polar modifier to the lithium initiator to be within the range of about 0.25:1 to about 3:1. It is generally most preferred for the molar ratio of polar modifier to the lithium initiator to be within the range of about 0.5:1 to about 3:2.

The polymerization can optionally be conducted utilizing an oligomeric oxolanyl alkane as the modifier. Such oligomeric oxolanyl alkanes will typically be of a structural formula selected from the group consisting of:

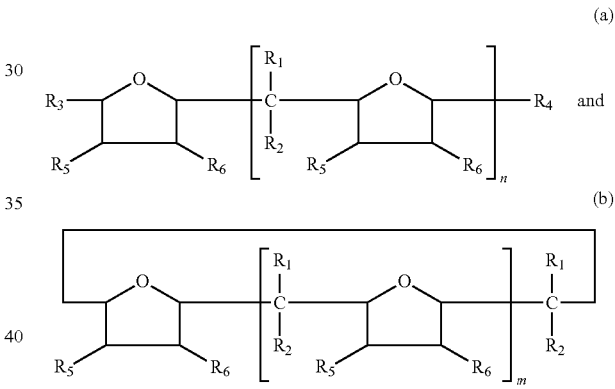

wherein n represents an integer from 1 to 5, wherein m represents an integer from 3 to 5, wherein $R_1$, $R_2$, $R_3$, $R_4$, $R_5$, and $R_6$ can be the same or different, and wherein $R_1$, $R_2$, $R_3$, $R_4$, $R_5$, and $R_6$ represent a member selected from the group consisting of hydrogen atoms and alkyl groups containing from 1 to about 8 carbon atoms. It is typically preferred for $R_1$, $R_2$, $R_3$, $R_4$, $R_5$, and $R_6$ represent a member selected from the group consisting of hydrogen atoms and alkyl groups containing from 1 to 4 carbon atoms.

The polymerization temperature utilized can vary over a broad range of from about −20° C. to about 180° C. In most cases, a polymerization temperature within the range of about 30° C. to about 125° C. will be utilized. It is typically preferred for the polymerization temperature to be within the range of about 45° C. to about 100° C. It is typically most preferred for the polymerization temperature to be within the range of about 60° C. to about 90° C. The pressure used will normally be sufficient to maintain a substantially liquid phase under the conditions of the polymerization reaction.

The polymerization will be allowed to continue until essentially all of the monomer has been exhausted. In other words, the polymerization is allowed to run to completion. Incremental addition, or a chain transfer agent, may be used in order to avoid excessive gel formation. Such minor modifications are within the skill of the artisan. Since a lithium catalyst is employed to polymerize the monomer, a living polymer is produced. After the polymerization has been completed, the functionalizing agent of this invention is added to the living polymer. The polymerization will typically be carried out to a high level of conversion. The level of monomer conversion will typically be at least 90% and will preferably be at least 95%. It is normally more preferred for the level of monomer conversion to be at least about 98%.

Functionalized living rubbery polymers can also be further functionalized with the boron containing functionalizing agents of this invention. This is accomplished by simply adding the functionalizing agent to the functionalized elastomer before killing its living lithium chain ends. Such functionalized rubbery polymers can be synthesized by polymerizing a functionalized monomer into the rubbery polymer. Such functionalized elastomers are disclosed by U.S. Pat. No. 6,627,721, U.S. Pat. No. 6,664,328, U.S. Pat. No. 6,693,160, U.S. Pat. No. 6,812,307 and U.S. Pat. No. 7,041,761. The teachings of U.S. Pat. No. 6,627,721, U.S. Pat. No. 6,664,328, U.S. Pat. No. 6,693,160, U.S. Pat. No. 6,812,307 and U.S. Pat. No. 7,041,761 are incorporated herein by reference for the purpose of disclosing functionalized elastomers that can be further functionalized with the boron containing functionalizing agents of this invention.

The functionalizing agent is normally added to the cement of the living rubbery polymer made by anionic polymerization. This can be accomplished by simply mixing the functionalizing agent into a solution of the living rubbery polymer under conditions of agitation. The functionalizing agent will readily react with the living lithium chains ends at ambient temperature. As has been explained, the molar ratio of functionalizing agent to living lithium chain ends will normally be within the range of 0.7:1 to 1.1:1 and will more typically be within the range of 0.9:1 to 1.02:1. It is preferred for the molar ratio of functionalizing agent to living lithium chain ends to be within the range of 0.99:1 to 1.01:1.

It should be noted that functionalizing the living rubbery polymer does not necessarily kill its lithium moieties that are capable of initiating further polymerization. Accordingly, after being functionalized a terminating agent is typically added. The terminating agent will typically be an alcohol or a coupling agent. For example, a tin halide and/or silicon halide can be used as a coupling agent. The tin halide and/or the silicon halide are continuously added in cases where asymmetrical coupling is desired. This continuous addition of tin coupling agent and/or the silicon coupling agent is normally done in a reaction zone separate from the zone where the bulk of the polymerization is occurring. The coupling agents will normally be added in a separate reaction vessel after the desired degree of conversion has been attained. The coupling agents can be added in a hydrocarbon solution, e.g., in cyclohexane, to the polymerization admixture with suitable mixing for distribution and reaction. In other words, the coupling will typically be added only after a high degree of conversion has already been attained. For instance, the coupling agent will normally be added only after a monomer conversion of greater than about 85 percent has been realized. It will typically be preferred for the monomer conversion to reach at least about 90 percent before the coupling agent is added.

The tin halides used as coupling agents will normally be tin tetrahalides, such as tin tetrachloride, tin tetrabromide, tin tetrafluoride or tin tetraiodide. However, tin trihalides can also optionally be used. Polymers coupled with tin trihalides having a maximum of three arms. This is, of course, in contrast to polymers coupled with tin tetrahalides which have a maximum of four arms. To induce a higher level of branching, tin tetrahalides are normally preferred. As a general rule, tin tetrachloride is most preferred.

The silicon coupling agents that can be used will normally be silicon tetrahalides, such as silicon tetrachloride, silicon tetrabromide, silicon tetrafluoride or silicon tetraiodide. However, silicon trihalides can also optionally be used. Polymers coupled with silicon trihalides having a maximum of three arms. This is, of course, in contrast to polymers coupled with silicon tetrahalides which have a maximum of four arms. To induce a higher level of branching, silicon tetrahalides are normally preferred. As a general rule, silicon tetrachloride is most preferred of the silicon coupling agents.

A combination of a tin halide and a silicon halide can optionally be used to couple the rubbery polymer. By using such a combination of tin and silicon coupling agents improved properties for tire rubbers, such as lower hysteresis, can be attained. It is particularly desirable to utilize a combination of tin and silicon coupling agents in tire tread compounds that contain both silica and carbon black. In such cases, the molar ratio of the tin halide to the silicon halide employed in coupling the rubbery polymer will normally be within the range of 20:80 to 95:5. The molar ratio of the tin halide to the silicon halide employed in coupling the rubbery polymer will more typically be within the range of 40:60 to 90:10. The molar ratio of the tin halide to the silicon halide employed in coupling the rubbery polymer will preferably be within the range of 60:40 to 85:15. The molar ratio of the tin halide to the silicon halide employed in coupling the rubbery polymer will most preferably be within the range of 65:35 to 80:20.

Broadly, and exemplary, a range of about 0.01 to 4.5 milliequivalents of tin coupling agent (tin halide and silicon halide) can be employed per 100 grams of the rubbery polymer. It is normally preferred to utilize about 0.01 to about 1.5 milliequivalents of the coupling agent per 100 grams of polymer to obtain the desired Mooney viscosity. The larger quantities tend to result in production of polymers containing terminally reactive groups or insufficient coupling. One equivalent of tin coupling agent per equivalent of lithium is considered an optimum amount for maximum branching. For instance, if a mixture tin tetrahalide and silicon tetrahalide is used as the coupling agent, one mole of the coupling agent would be utilized per four moles of live lithium ends. In cases where a mixture of tin trihalide and silicon trihalide is used as the coupling agent, one mole of the coupling agent will optimally be utilized for every three moles of live lithium ends. The coupling agent can be added in a hydrocarbon solution, e.g., in cyclohexane, to the polymerization admixture in the reactor with suitable mixing for distribution and reaction.

After coupling has optionally been completed, a tertiary chelating alkyl 1,2-ethylene diamine or a metal salt of a cyclic alcohol can optionally be added to the polymer cement to stabilize the coupled rubbery polymer. The tertiary chelating amines that can be used are normally chelating alkyl diamines of the structural formula:

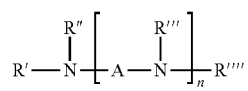

wherein n represents an integer from 1 to about 6, wherein A represents an alkylene group containing from 1 to about 6 carbon atoms and wherein R', R", R'" and R"" can be the same or different and represent alkyl groups containing from 1 to about 6 carbon atoms. The alkylene group A is of the formula —(—CH$_2$—)$_m$ wherein m is an integer from 1 to about 6. The alkylene group will typically contain from 1 to 4 carbon atoms (m will be 1 to 4) and will preferably contain 2 carbon atoms. In most cases, n will be an integer from 1 to about 3 with it being preferred for n to be 1. It is preferred for R', R", R'" and R"" to represent alkyl groups which contain from 1 to 3 carbon atoms. In most cases, R', R", R'" and R"" will represent methyl groups.

In most cases, from about 0.01 phr (parts by weight per 100 parts by weight of dry rubber) to about 2 phr of the chelating alkyl 1,2-ethylene diamine or metal salt of the cyclic alcohol will be added to the polymer cement to stabilize the rubbery polymer. Typically, from about 0.05 phr to about 1 phr of the chelating alkyl 1,2-ethylene diamine or metal salt of the cyclic alcohol will be added. More typically, from about 0.1 phr to about 0.6 phr of the chelating alkyl 1,2-ethylene diamine or the metal salt of the cyclic alcohol will be added to the polymer cement to stabilize the rubbery polymer.

The terminating agents that can be used to stop the polymerization and to "terminate" the living rubbery polymer include tin monohalides, silicon monohalides, N,N,N',N'-tetradialkyldiamino-benzophenones (such as tetramethyldiaminobenzophenone and the like), N,N-dialkylamino-benzaldehydes (such as dimethylaminobenzaldehyde and the like), 1,3-dialkyl-2-imidazolidinones (such as 1,3-dimethyl-2-imidazolidinone and the like), 1-alkyl substituted pyrrolidinones; 1-aryl substituted pyrrolidinones, dialkyl-dicycloalkyl-carbodiimides containing from about 5 to about 20 carbon atoms, and dicycloalkyl-carbodiimides containing from about 5 to about 20 carbon atoms.

After the termination step, and optionally the stabilization step, has been completed, the rubbery polymer can be recovered from the organic solvent. The coupled rubbery polymer can be recovered from the organic solvent and residue by means such as chemical (alcohol) coagulation, thermal desolventization, or other suitable method. For instance, it is often desirable to precipitate the rubbery polymer from the organic solvent by the addition of lower alcohols containing from about 1 to about 4 carbon atoms to the polymer solution. Suitable lower alcohols for precipitation of the rubber from the polymer cement include methanol, ethanol, isopropyl alcohol, normal-propyl alcohol and t-butyl alcohol. The utilization of lower alcohols to precipitate the rubbery polymer from the polymer cement also "terminates" any remaining living polymer by inactivating lithium end groups. After the coupled rubbery polymer is recovered from the solution, steam-stripping can be employed to reduce the level of volatile organic compounds in the coupled rubbery polymer. Additionally, the organic solvent can be removed from the rubbery polymer by drum drying, extruder drying, vacuum drying, and the like.

The polymers of the present invention can be used alone or in combination with other elastomers to prepare a rubber compounds, such as a tire treadstock, sidewall stock or other tire component stock compounds. In a tire of the invention, at least one such component is produced from a vulcanizable elastomeric or rubber composition. For example, the rubbery polymer made by the process of this invention can be blended with any conventionally employed treadstock rubber which includes natural rubber, synthetic rubber and blends thereof. Such rubbers are well known to those skilled in the art and include synthetic polyisoprene rubber, styrene/butadiene rubber (SBR), polybutadiene, butyl rubber, Neoprene, ethylene/propylene rubber, ethylene/propylene/diene rubber (EPDM), acrylonitrile/butadiene rubber (NBR), silicone rubber, the fluoroelastomers, ethylene acrylic rubber, ethylene vinyl acetate copolymer (EVA), epichlorohydrin rubbers, chlorinated polyethylene rubbers, chlorosulfonated polyethylene rubbers, hydrogenated nitrile rubber, tetrafluoroethylene/propylene rubber and the like.

When the rubbery polymers made by the process of the present invention are blended with conventional rubbers, the amounts can vary widely such as between 10 and 99 percent by weight. In any case, tires made with synthetic rubbers that are synthesized utilizing the technique of this invention exhibit decreased rolling resistance. The greatest benefits are realized in cases where the tire tread compound is made with the rubbery polymer synthesized utilizing the technique of this invention. However, benefits can also by attained in cases where at least one structural element of the tire, such as subtread, sidewalls, body ply skim, or bead filler, is comprised of the rubbery.

The synthetic rubbers made in accordance with this invention can be compounded with carbon black in amounts ranging from about 5 to about 100 phr (parts by weight per 100 parts by weight of rubber), with about 5 to about 80 phr being preferred, and with about 40 to about 70 phr being more preferred. The carbon blacks may include any of the commonly available, commercially-produced carbon blacks but those having a surface area (EMSA) of at least 20 m2/g and more preferably at least 35 m2/g up to 200 m2/g or higher are preferred. Surface area values used in this application are those determined by ASTM test D-1765 using the cetyltrimethyl-ammonium bromide (CTAB) technique. Among the useful carbon blacks are furnace black, channel blacks and lamp blacks. More specifically, examples of the carbon blacks include super abrasion furnace (SAF) blacks, high abrasion furnace (HAF) blacks, fast extrusion furnace (FEF) blacks, fine furnace (FF) blacks, intermediate super abrasion furnace (ISAF) blacks, semi-reinforcing furnace (SRF) blacks, medium processing channel blacks, hard processing channel blacks and conducting channel blacks. Other carbon blacks which may be utilized include acetylene blacks. Mixtures of two or more of the above blacks can be used in preparing the carbon black products of the invention. Typical values for surface areas of usable carbon blacks are summarized in the following table.

| Carbon Black | |
| --- | --- |
| ASTM Designation (D-1765-82a) | Surface Area (D-3765) |
| N-110 | 126 m$^2$/g |
| N-220 | 111 m$^2$/g |
| N-330 | 83 m$^2$/g |
| N-339 | 95 m$^2$/g |
| N-550 | 42 m$^2$/g |
| N-660 | 35 m$^2$/g |

The carbon blacks utilized in the preparation of rubber compounds may be in pelletized form or an unpelletized flocculent mass. Preferably, for more uniform mixing, unpelletized carbon black is preferred. The reinforced rubber compounds can be cured in a conventional manner with about 0.5 to about 4 phr of known vulcanizing agents. For example, sulfur or peroxide-based curing systems may be employed. For a general disclosure of suitable vulcanizing agents one can refer to Kirk-Othmer, Encyclopedia of Chemical Technology, 3rd ed., Wiley Interscience, N.Y. 1982, Vol. 20, pp. 365-468, particularly "Vulcanization Agents and Auxiliary Materials" pp. 390-402. Vulcanizing agents can, of curse, be used alone or in combination. Vulcanizable elastomeric or rubber compositions can be prepared by compounding or mixing the polymers thereof with carbon black and other conventional rubber additives such as fillers, plasticizers, antioxidants, curing agents and the like, using standard rubber mixing equipment and procedures and conventional amounts of such additives.

Tire tread formulations can be made by utilizing one or more rubbery polymers that have been functionalized with the boron containing functionalizing agents of this invention. For instance, useful tread formulations for truck tires can be made by blending natural rubber and styrene-butadiene rubber that has been functionalized in accordance with this invention. Tread formulations for automobile tires can be beneficially made by blending high cis-1,4-polybutadiene rubber into styrene-butadiene rubber that has been functionalized in accordance with this invention.

This invention is illustrated by the following examples that are merely for the purpose of illustration and are not to be regarded as limiting the scope of the invention or the manner in which it can be practiced. Unless specifically indicated otherwise, parts and percentages are given by weight.

Example 1

Synthesis of P-Benzyliminephenylboronic Acid Pinacol Ester

In the first step of this synthesis procedure 1 gram of 5 Å molecular sieves was added to a 50 ml round bottom flask that was equipped with a stirbar. Then, 1.00 grams (4.56 mmol) of 4-aminophenylboronic acid pinacol ester was added to the flask and it was sealed with a rubber septum. The reaction flask was then evacuated and backfilled with dry nitrogen three times. Following the last evacuation, the flask was placed under a stream of nitrogen. Then, 10 ml of anhydrous toluene was added to the flask with a syringe, and the contents of the flask were stirred. Under conditions of rapid stirring, 0.46 ml (4.58 mmol) of benzaldehyde was added dropwise via syringe.

Once the benzaldehyde was added, the reaction flask was equipped with a reflux condenser under nitrogen overnight. The reaction flask was cooled to room temperature and the contents were filtered. An additional 10 ml of anhydrous toluene was added to facilitate the filtration. The filtrate was filtered a second time and collected. The collected filtrate was concentrated via rotary evaporation to yield a pale yellow, low melting solid (1.34 grams, 96%). This solid was isolated in 98% purity, as characterized by $^1$H NMR spectroscopy and was not further purified.

Example 2

Synthesis of Functionalized Polybutdiene Rubber

In this experiment a four-ounce glass polymerization bottle was stored in an over at 160° C. and cooled under a stream of dry nitrogen. The bottle was then sealed with a metal screw cap with a septum lining. Then, 80 ml of a 15% by weight solution of 1,3-butadiene in hexane was charged into the polymerization bottle as a premix. The premix had been circulated through a drying column consisting of silica gel and 3 Å molecular sieves for 72 hours prior to utilization. Then, the polymerization bottle was charged with 0.50 ml of n-butyl-lithium via syringe to initiate polymerization.

The bottles were then tumbled in a heated water bath that was maintained at a temperature of 65° C. for 1 hour. The polymerization bottle was then removed from the water bath and the p-benzyliminephenylboronic acid pinacol ester synthesized in Example 1 was added as a solution in tetrahydrofuran to functionalize the polybutadiene rubber. The bottle was shaken and allowed to stand at room temperature for 30 minutes.

Roughly ⅔ of the contents of the polymerization bottle was poured into an aluminum pan and dried. The pan-dried sample was analyzed by GPC. Acetone was added to the remaining cement in each bottle with occasional stirring. After addition of an equal volume of acetone, the contents of the bottle became milky white in color due to the polymer crashing out of solution. The bottle was then placed in a centrifuge for 30 minutes, suring which the polymer settled to the bottom of the bottle. The polymer was carefully extracted via pipet and dried in vacuo overnight. The resulting precipitated polymer sample was analyzed by $^1$H NMR spectroscopy.

Comparative Example 3

In this experiment conventional styrene-butadiene rubber (SBR) was synthesized in a one gallon (3.8 liter) reactor utilizing the same general procedure as was used in Example 2, except that a 10% by weight 2,6-di-tert-butyl-p-cresol in isopropanol solution was added to the polymerization bottle in place of the p-benzyliminephenylboronic acid pinacol ester to terminate polymerization.

Example 4 and Comparative Example 5

In this experiment functionalized styrene-butadiene rubber make utilizing the technique of this invention and the conventional styrene-butadiene rubber made in Comparative Example 3 were compounded, cured, and evaluated to determine physical properties. The properties of these styrene-butadiene rubber (SBR) samples after being cured at 160° C. for 14 minutes are reported in Table 1.

TABLE 1

| | Functionalized SBR | Conventional SBR |
|---|---|---|
| G' (15%, 0.83 Hz, 100° C.) | 0.206 MPa | 0.14 Mpa |
| T25 | 4.7 min | 2.82 min |
| T90 | 10.08 min | 9.45 min |
| G' (1%, 11 Hz, 40° C.) | 3.457 MPa | 5.594 MPa |
| Tan Delta (1%, 11 Hz, 40° C.) | 0.087 | 0.106 |
| G' (1%, 11 Hz, 100° C.) | 2.862 MPa | 3.953 MPa |
| G' (5%, 11 Hz, 100° C.) | 2.139 MPa | 2.566 MPa |
| G' (10%, 11 Hz, 100° C.) | 1.761 MPa | 1.923 MPa |
| Tan Delta (10%, 11 Hz, 100° C.) | 0.116 | 0.163 |
| G' (50%, 11 Hz, 100° C.) | 1.046 MPa | 0.985 MPa |
| J" (10%, 11 Hz, 100° C.) | 0.065 1/MPA | 0.083 1/MPa |
| 100% Modulus | 1.6 MPa | 1.6 MPa |
| 300% Modulus | 8.04 MPa | 6.45 MPa |
| Tensile Strength | 15.78 MPa | 9.18 MPa |
| Elongation at Break | 498% | 419% |
| Hardness at RT | 64.2 | 69.1 |
| Hardness at 100° C. | 60.1 | 61.4 |
| Rebound at RT | 44.5 | 39.4 |
| Rebound at 100° C. | 65.3 | 55.8 |
| Specific Gravity | 1.166 g/cm$^3$ | 1.168 g/cm$^3$ |
| Energy | 79 | 43 |

While certain representative embodiments and details have been shown for the purpose of illustrating the subject invention, it will be apparent to those skilled in this art that various changes and modifications can be made therein without departing from the scope of the subject invention.

What is claimed is:

1. A functionalizing agent which is comprised of a boron containing compound having a structural formula selected from the group consisting of:

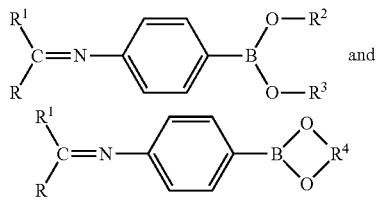

and wherein R is selected from the group consisting of hydrogen atoms, alkyl groups and aryl groups, wherein $R^1$, $R^2$, and $R^3$ can be the same or different and are selected from the group consisting of alkyl groups, and aryl groups, and wherein $R^4$ represents an aromatic bridging group that contains from 6 to 30 carbon atoms.

2. A functionalizing agent as specified in claim 1 wherein R represents a hydrogen atom.

3. A functionalizing agent as specified in claim 2 wherein $R^1$ represents a phenyl group.

4. A functionalizing agent as specified in claim 1 wherein said functionalizing agent is of the structural formula:

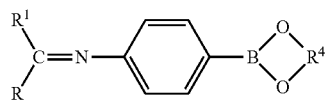

wherein $R^4$ represents an aromatic bridging group that contains from 6 to 30 carbon atoms.

5. A functionalizing agent as specified in claim 4 wherein $R^1$ represents a phenyl group.

6. A functionalizing agent as specified in claim 1 wherein $R^4$ represents an aromatic bridging group that contains from 6 to 20 carbon atoms.

7. A functionalizing agent as specified in claim 1 wherein $R^4$ represents an aromatic bridging group that contains from 6 to 12 carbon atoms.

8. A functionalizing agent as specified in claim 1 wherein the aromatic bridging group includes an aromatic ring structure selected from the group consisting of a benzene ring, a naphthalene ring structure, an anthracene ring structure, a phenanthrene ring structure, a pentalene ring structure, an indene ring structure, an azulene ring structure, a heptalene ring structure, a biphenylene ring structure, a s-indacene ring structure, a fluorene ring structure, an acenaphthylene ring structure, an acephenanthrylene ring structure, a chrysene ring structure, a pyrene ring structure, a naphthacene ring structure, a triphenylmethane ring structure, a tetraphenylmethane ring structure, a stilbene ring structure, and a biphenyl ring structure.

9. A functionalizing agent as specified in claim 1 wherein $R^4$ represents an aromatic bridging group having a structural formula selected from the group consisting of

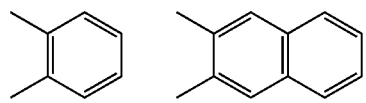

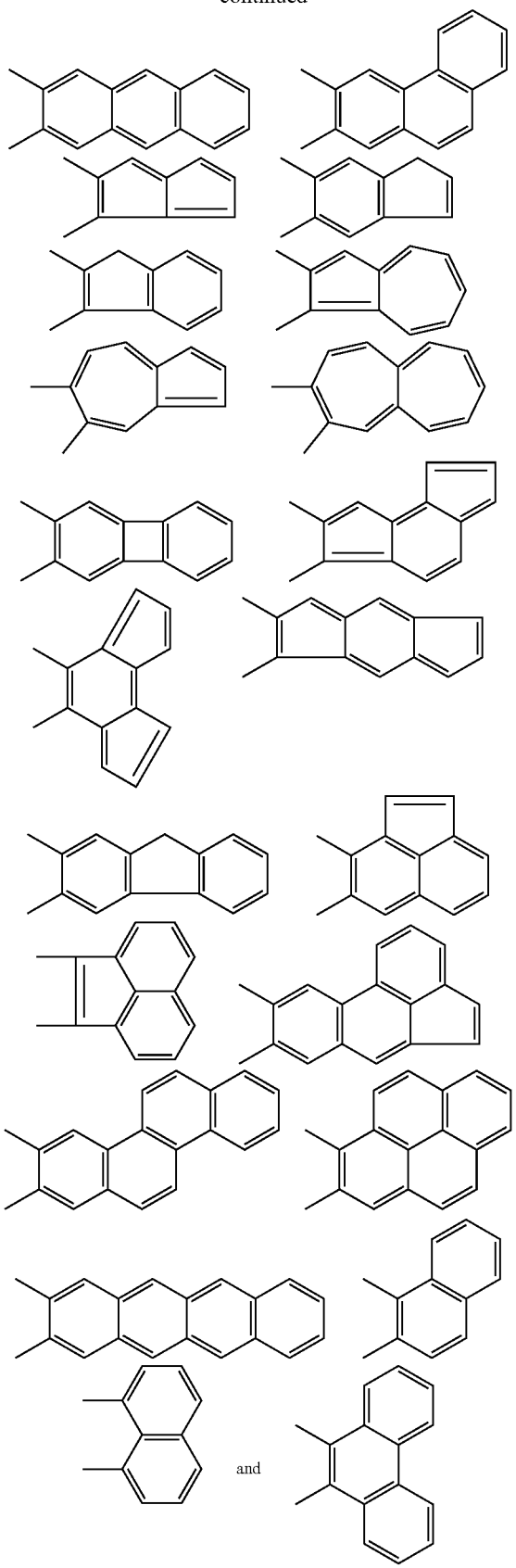

and and wherein R represents a hydrogen atom.

10. A functionalizing agent as specified in claim 9 wherein $R^1$ represents a phenyl group.

11. A functionalizing agent as specified in claim 1 wherein said functionalizing agent is of the structural formula:

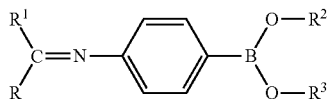

wherein $R^2$ and $R^3$ can be the same or different and are selected from the group consisting of alkyl groups containing from 1 to about 20 carbon atoms and aryl groups containing from 5 to about 20 carbon atoms.

12. A functionalizing agent as specified in claim 11 wherein $R^2$ and $R^3$ can be the same or different and are selected from the group consisting of alkyl groups containing from 1 to 8 carbon atoms and aryl groups containing from 6 to about 12 carbon atoms.

13. A functionalizing agent as specified in claim 11 wherein $R^2$ and $R^3$ can be the same or different and represent alkyl groups containing from 1 to 4 carbon atoms.

14. A functionalizing agent as specified in claim 11 wherein $R^2$ and $R^3$ represent methyl groups.

15. A functionalizing agent as specified in claim 1 wherein $R^4$ represents an aromatic bridging group having the structural formula:

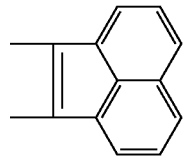

wherein R represents a hydrogen atom and wherein $R^1$ represents a phenyl group.

16. A functionalizing agent as specified in claim 1 wherein $R^4$ represents an aromatic bridging group having the structural formula:

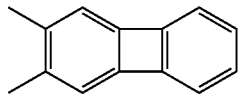

wherein R represents a hydrogen atom and wherein $R^1$ represents a phenyl group.

17. A process for synthesizing the boron containing functionalizing agent of claim 1, comprising reacting a boronic ester with a carbonyl compound to produce the boron containing functionalizing agent.

18. The process for synthesizing a boron containing functionalizing agent as specified in claim 17 wherein the boron containing functionalizing agent is of the structural formula:

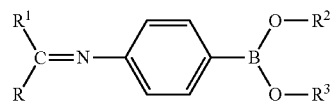

wherein R is selected from the group consisting of hydrogen atoms, alkyl groups and aryl groups, wherein $R^1$, $R^2$, and $R^3$ can be the same or different and are selected from the group consisting of alkyl groups and aryl groups.

19. The process for synthesizing a boron containing functionalizing agent as specified in claim 17 wherein the boron containing functionalizing agent is of the structural formula:

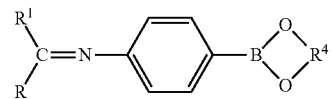

wherein R is selected from the group consisting of hydrogen atoms, alkyl groups and aryl groups, wherein $R^1$ is selected from the group consisting of alkyl groups and aryl groups, and wherein $R^4$ represents an aromatic bridging group that contains from 6 to 30 carbon atoms.

20. The process for synthesizing a boron containing functionalizing agent as specified in claim 19 wherein $R^4$ represents an aromatic bridging group that contains from 6 to 12 carbon atoms.

* * * * *